United States Patent [19]
Kossovsky et al.

[11] Patent Number: 5,441,739
[45] Date of Patent: Aug. 15, 1995

[54] REDUCED AND CONTROLLED SURFACE BINDING OF BIOLOGICALLY ACTIVE MOLECULES

[75] Inventors: Nir Kossovsky; Andrew E. Gelman, both of Los Angeles; Edward E. Sponsler, Burbank, all of Calif.

[73] Assignee: The Regents of the University of California, Oakland, Calif.

[21] Appl. No.: 29,896

[22] Filed: Mar. 11, 1993

Related U.S. Application Data

[63] Continuation-in-part of Ser. No. 199, Jan. 4, 1993, Pat. No. 5,334,394, which is a continuation-in-part of Ser. No. 690,601, Apr. 24, 1991, Pat. No. 5,178,882, which is a continuation-in-part of Ser. No. 542,255, Jun. 22, 1990, Pat. No. 5,219,577.

[51] Int. Cl.$^6$ ............................................. A61K 9/00
[52] U.S. Cl. ................................... 424/400; 424/422; 424/423; 424/461; 424/493; 424/494; 600/30; 604/891.1; 604/8; 604/43; 604/327; 604/403; 606/1; 606/14; 607/2
[58] Field of Search ............... 424/461, 479, 480, 490, 424/493, 494, 400

[56] References Cited

U.S. PATENT DOCUMENTS

| | | | |
|---|---|---|---|
| 4,452,773 | 6/1984 | Molday | 424/1.1 |
| 4,906,237 | 3/1990 | Johansson et al. | 604/265 |
| 4,994,069 | 2/1991 | Ritchart et al. | 606/191 |
| 5,178,882 | 1/1993 | Kossovsky | 424/494 |

FOREIGN PATENT DOCUMENTS 1252950  4/1989  Canada .

OTHER PUBLICATIONS

Kossovsky, N. et al: "Nanocrystalline Epstein-Barr Virus Decoys," Jour. Appl. Biomaterials, vol. 2, 251-259 (1991).
Levine, H. and Slade, L.: "Another View of Trehalose for Drying and Stabilizing Biological Materials," BioPharm, (May 1992) pp. 36-40.
Crowe, J. H. et al.: "Interactions of sugars with membranes," Biochimica et Biophisica Acta, 947 (1988) 367-384.
Fleminger, G. et al.: "Effect of polyethylene glycol on the non-specific adsorption of proteins to Eupergit C and agarose," Jour. Chromatography, 510 (1990) pp. 271-279.
Bruin, G. J. M., et al.: "Performance of Carbohydrate-Modified Fused-Silica Capillaries for the Separation of Proteins by Zone Electrophoresis," Jour. Chromatography, 480 (1989) pp. 339-349.
Hjerten, S.: "Free Zone Electrphoresis," Chromatographic Reviews, 9 (1967) pp. 122-219.
Hjerten, S.: "High-Performance Elctrophoresis Elimination of Electroendosmosis and Solute Adsorption," Jour. Chromatography, 347 (1985) pp. 191-198.
McCormick, R. M.: "Capillary Zone Electrophoretic Separation of Peptides and Proteins Using Low pH Buffers in Modified Silica Capillaries," Anal. Chem. (1988), 60, pp. 2322-2328.
Gordon, M. J. et al.: "Protocol for Resolving Protein Mixtures in Capillary Zone Electrophoresis," Anal. Chem. (1991), 63, pp. 69-72.

*Primary Examiner*—Thurman K. Page
*Assistant Examiner*—James M. Spear
*Attorney, Agent, or Firm*—Poms, Smith, Lande & Rose

[57] ABSTRACT

Articles of manufacture which are adapted for use in contact with one or more biologically active agents are coated with a glassy carbohydrate film. The glassy film provides a reduced surface energy coating which exhibits a reduced degree of binding with biologically active agents. Methods for applying the glassy carbohydrate film are disclosed wherein the glassy film is adsorbed directly onto the article surface. The coated articles are for use both in vitro and in vivo where contact with biologically active agents is expected.

8 Claims, 1 Drawing Sheet

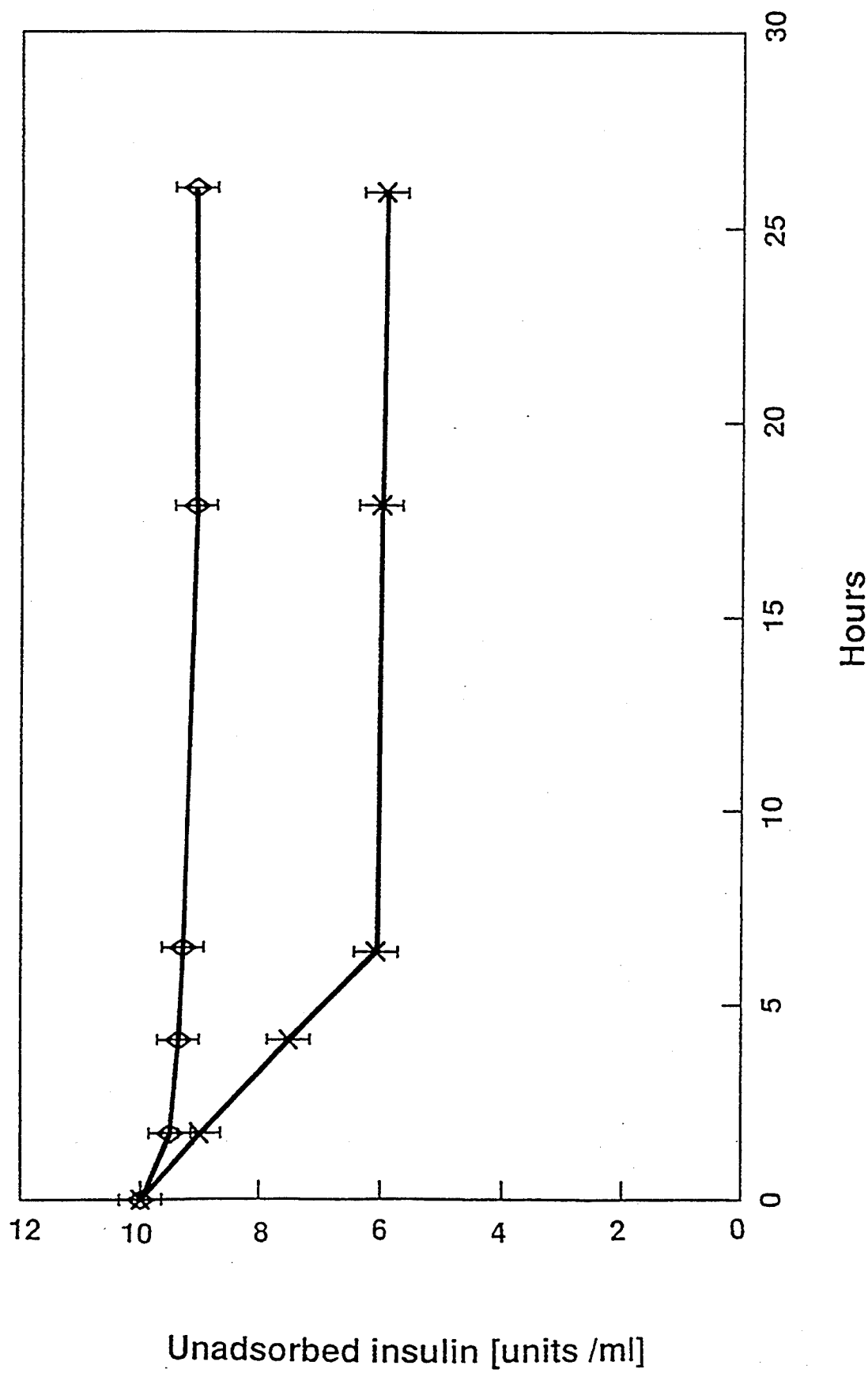

REDUCED AND CONTROLLED SURFACE BINDING OF BIOLOGICALLY ACTIVE MOLECULES

This is a continuation-in-part of application, Ser. No. 8/000,199, which was filed on Jan. 4, 1993, now U.S. Pat. No. 5,334,394 which is a continuation-in-part of application, Ser. No. 07/690,601, filed Apr. 24, 1991, now U.S. Pat. No. 5,178,882, which is a continuation-in-part of application, Ser. No. 07/542,255, which was filed on Jun. 22, 1990, now U.S. Pat. No. 5,219,577.

BACKGROUND OF THE INVENTION

1. Field of the Invention

The present invention relates generally to articles which are designed to be in contact with biologically active agents. Such articles include implant devices and other structures which are designed to be utilized in vivo. Such articles also include containers, supports, and transport systems wherein biologically active agents are in continual contact with the surfaces of the article. More particularly, the present invention relates to reducing and thereby controlling the degree to which biologically active agents bind to the surfaces of such articles.

2. Description of Related Art

Most biologically active agents interact with other molecules present on either surfaces or membranes. In fact, the effectiveness of many biological systems is dependent on the presence of certain intrinsic binding properties between biologically active agents and biological surfaces. For example, biological surfaces, such as endothelial linings or receptor-embedded cell membranes, incorporate high affinity (energy) binding properties to achieve optimal biological function. Although the binding properties of biologically active agents is essential for proper biological function, there are many situations where binding of these biologically active agents to non-biological surfaces presents a problem. For example, the coagulation protein factor XII is a biologically active agent which binds to healthy vascular endothelial cells. Protein factor XII plays an important role in the naturally occurring coagulation process. However, when protein factor XII binds to the surface of an implanted biomaterial, the result may be a thrombotic or thromboembolic complication of the prosthetic device.

Other situations where reduced surface binding of biologically active agents would be desirable include vessels used to transport biologically active agents. In these situations, binding of the agent to the wall of the transport container results in reduced yield of the transported product. In addition, reduced binding would be desirable in a vascular prosthesis where interactions of biologically active agents can promote complications and reduce the medical utility of the device. For example, it would be desirable to reduce surface binding of biologically active agents to hip prostheses where the binding of such agents can result in denaturization of the agents and the initiation of an inflammatory reaction clinically associated with pain and reduced utility of the device.

Another situation where reduced and thereby controlled surface binding of biologically active agents would be desirable includes the fabrication of biological opto-electronic devices. These devices would provide electronic output from electron transporting biologically active molecules responding to photoelectric, thermal, or other environmental stimulus. To fabricate these devices, only limited numbers of biologically active molecules would be deposited ideally on a solid support. Moreover, the reduced and thereby controlled binding of the biologically active molecules would ideally not result in conformational denaturation of the molecules.

The non-biological materials which are commonly used in the manufacture of biomedical and food service devices include polymers, ceramics and metals, most of which have high surface energies. These high surface energies result frequently in increased binding of biologically active molecules in situations, such as those described above, where such binding is undesirable. Accordingly, it would be desirable to provide a treatment for the surfaces of such non-biological materials which would effectively reduce the surface energy and thereby decrease undesirable binding of biologically active agents thereto.

Over the years, various materials have been developed for use as surface modifying agents which reduce the binding of biologically active agents to their surfaces. Examples include polymers, such as silicone, polystyrene, polyethylene and polytetrafluoroethylene. All of these materials have low surface energies. Accordingly, the binding affinities between these materials and biologically active agents is reduced. These materials are generally used in bulk form, i.e., the entire device is made from the materials.

More recently, different alcohol based compounds have been either physically adsorbed or chemically bonded to the surface of non-biological materials to reduce the subsequent surface binding of biologically active agents. Among the more commonly used are polyethylene glycol and sodium heparin. While affording improved resistance to absorption of proteins and other biologically active agents, these two exemplary materials are each subject to their own specific problems. For example, non-biological surfaces, such as immunoaffinity chromatography columns and electrophoretic capillaries, have been coated with polyethylene glycol. Although such coatings have reduced binding of biologically active agents, the nephrotoxic effects of polyethylene glycol are well documented. Further, binding of polyethylene glycol to the non-biological surface is possible only through various forms of covalent chemistry.

Sodium heparin is a well-recognized anti-coagulation factor whose use entails correlative physiological effects. Most often, sodium heparin is covalently bound directly to the non-biological surface or indirectly through various carbon chain extenders. In addition, sodium heparin has been physically absorbed onto the non-biological surface. Other surface modification techniques have involved the coating of electrophoretic capillaries with phosphate moieties and conventional silanes and polyacrylimides.

Other attempts at reducing the surface activity of non-biological materials have involved the covalent bonding of maltose to silica substrates wherein an additional silicone-based intermediate moiety (3-aminopropyltriethoxysilane) is covalently bound to both the fused-silica capillary walls and the disaccharide. In another procedure, cellulose has been absorbed onto non-biological surfaces. Specifically, methylcellulose has been used to coat the inside of quartz electrophoresis tubes to reduce or eliminate electroendosmosis. The protocol used in applying the methylcellulose coating involves three steps. First, the electrophoresis tube is washed with detergent. The possibility of detergent residues present on the quartz surface is not desirable since it may block carbohydrate adsorption. The second step involves addition of formaldehyde and formic acid to the methylcellulose solution to catalyze the cross-linking of the carbohydrate molecules which are present in the coating. Finally, the quartz tube is heated between applications of the methylcellulose.

There presently is a need to provide a simple, quick, and efficient technique for reducing the surface energy of articles which are designed for use in contact with biologically active agents. The technique should be capable of reducing surface energy levels sufficiently to reduce and thereby control the binding of biologically active agents to the article's surface.

SUMMARY OF THE INVENTION

In accordance with the present invention, a method is provided for reducing the surface energy of materials which are used in articles that are designed for contact with biologically active agents. The present invention involves coating the surface of the article with a relatively low energy glassy carbohydrate film. The carbohydrate film has a surface energy which is well below the surface energy of many non-biological materials, such as metals, ceramics, and certain polymers. The glassy carbohydrate film provides a sufficient reduction in surface energy to reduce the binding energy between the surface and biologically active agents.

As a feature of the present invention, the glassy carbohydrate film is simply applied to the article surface by adsorption. An essential aspect of the present invention is that the article surface must be substantially free of contaminating material. It was discovered that glassy carbohydrate films adsorb readily to article surfaces provided that the surfaces are contaminant free. The simplicity of adsorbing glassy carbohydrate films onto clean article surfaces makes the invention well suited for use in a wide variety of situations where it is desired to reduce the surface energy of a particular device or article of manufacture.

As a further feature of the present invention, carbohydrate films which are especially amenable to reducing surface energy were found to include cellobiose, trehalose, isomaltose, nystose, sucrose and related oligosaccharides. In addition to basic sugars, allosteric effectors may also be used alone or in combination with the basic sugars to provide an effective glassy carbohydrate film which provides substantial reductions in surface energy.

The above-discussed and many other features and attendant advantages of the present invention will become better understood by reference to the following detailed description when taken in conjunction with the accompanying drawing.

BRIEF DESCRIPTION OF THE DRAWING

The drawing is a graph of the adsorption isotherms showing the effectiveness of the present invention in reducing binding of insulin to the surface of borosilicate glass vials.

DETAILED DESCRIPTION OF THE PREFERRED EMBODIMENTS

The present invention has wide application to articles of manufacture which are used in contact with one or more biologically active agents. The articles may be designed for in vivo or in vitro use. Examples of articles designed for in vivo use which may be treated in accordance with the present invention include implant devices, such as a cardiac pacemaker, electrode, central nervous system fluid shunt, and infusion pump. Other articles which are designed for in vivo use which are amenable to treatment in accordance with the present invention include percutaneous electrodes and transcortical percutaneous orthopedic pins. Articles which are designed for in vitro use which may be treated in accordance with the present invention include containers for biologically active agents, transport devices and virtually any article or device which is designed to be in continual contact with solutions that contain biologically active agents. Examples are intravenous fluid solution bags, hypodermic syringes and needles, food processing conduits, pesticide applicators, and cans of motor oil.

The articles which may be treated in accordance with the present invention are made from metal, metal alloys, ceramics and polymers. Specific examples of metals and metal alloys include stainless steel, gold, silver, aluminum, silicon and titanium. Specific examples of ceramic materials include glass (sodium borosilicate and other types), aluminum oxide, silicon oxide, zirconium oxide, silicon nitride, and diamond. Polymer materials include polystyrene, polyethylene, polyacrylate, polymethylmethacrylate, polycarbonate, polyvinylchloride, polyurethane and silicone.

In accordance with the present invention, the surface of the article is coated with a glassy carbohydrate film. The glassy films are preferably made from sugars selected from the group of basic sugars, such as cellobiose, trehalose, isomaltose, nystose, and related oligosaccharides. In addition, the glassy film may be made from allosteric effectors such as pyridoxal-5-phosphate, or 2,3 phosphoglycerate. If desired, the glassy film may be made from a combination of basic sugars and one or more allosteric effectors.

In accordance with the present invention, it is essential that the surface of the article be free of contaminants prior to application of the glassy carbohydrate film. Any of the conventional techniques commonly used to provide ultra cleaning of surfaces may be used. These techniques include acid washing, washing with super critical fluids, or heating. Combinations of these methods, along with more sophisticated techniques such as plasma glow discharge cleaning, may be used. The particle cleaning technique used is not particularly important. What is important is that the surface to be coated be substantially contaminant free.

The coating of the clean article surface is accomplished by simple adsorption of the glassy film onto the ultra clean surface. As will be realized, it is necessary that the surface must remain clean until the carbohydrate film is applied. Ultra clean, high energy surfaces are very reactive and will bind with a wide variety of materials other than carbohydrates. Accordingly, it is necessary that the cleaned surface be maintained in a contaminant free environment until the glassy film is applied.

Any number of techniques may be utilized for applying the glassy film to the article surface. A convenient method involves simply immersing the article into a concentrated solution of the carbohydrate. Other techniques may be used, provided that they are capable of applying a uniform coating of glassy carbohydrate. The film thickness is not particularly important, so long as the underlying high energy surface is substantially covered. Film thicknesses on the order of less than 1 nanometer to 1 micron are suitable. The glassy film may also be applied as a pattern on the surface of the support material. Support material surfaces with patterns of glassy films thereon would be useful in more complex systems such as bio/opto-electric devices. Patterns of glassy films can be created using photoetching or other chemical/masking operations which are routinely used to create integrated circuits.

The present invention is particularly well suited for treating articles and devices which are used in vivo to reduce binding of biologically active agents within the mammalian body. However, the present invention may be used to coat any article wherein it is desired to reduce the binding energy between the article surface and biologically active agents. For example, various applications include the coating of articles such as bottles for the transportation of pharmacologic agents, tubing and bags containing pharmacologic agents for administration, implantable medical devices, tubing used to conduct biological fluids (e.g., extracorporeal hemodialysis and extracorporeal blood oxygenation). Also, articles such as primary stainless steel used in the food industry may be coated in accordance with the present invention. For example, conduits and tubing used to transport various prepared foods from preparation vats to the canning or bottling assembly line may be coated in accordance with the present invention to reduce binding of biologically active agents. Supports used to anchor biologically active molecules, such as support particles and beads, may also be coated.

The present invention is especially well suited for large scale operations where the simplicity of reducing surface activity by coating with glassy carbohydrate films is desirable. Further, the inexpensive nature of the carbohydrate coating process and the abundance of surface modifying carbohydrates makes the present invention especially well suited for commercial use. Further, the resulting glassy carbohydrate surface is a highly biocompatible surface which is glassy, water-like and relatively low in surface binding energy.

An example of an exemplary embodiment of the present invention wherein glass storage vessels are coated with a cellobiose coating is as follows:

Glass vials (4.0 ml.) were sonicated in 10 N hydrochloric acid for 20 minutes and rinsed liberally in high performance liquid chromatography (HPLC) grade water. The vials were then baked at 210° C. in a glassware oven for at least 18 hours before being cooled to 25° C. in a laminar flow hood under nitrogen gas. Half of the vials were then incubated with a 500 mM cellobiose solution overnight at 5° C. After incubation, both coated and non-coated vials were washed with sterile HPLC grade water three times. The vials were then allowed to dry in a laminar flow hood before insulin solutions were added.

To demonstrate the reduced surface binding of biologically active molecules to he cellobiose treated glass surface, the loss of insulin from solution was measured over time. Clean, heat treated, vials (both cellobiose coated and non-coated) were incubated with Novalin R recombinant insulin over a 24 hour time frame. A concentration of 10 units/ml of a pH 6.1 phosphate buffered saline solution was employed because of the good DEAE column sensitivity by HPLC. Unadsorbed insulin concentration was calculated from the integration of a 280 mn absorbing peak with an average retention time of three minutes. The mobile phase was a 20 mM acetic acid buffer (pH 4.5) with a linear 0–800 mM NaCl gradient over a 30 minutes interval at a flow rate of 1.0 ml/minute through a Waters R DEAE 5PW column. Determinations were taken in triplicate and averaged at times zero. 2, 4, 7, 18 and 27 hours. The Drawing is a graph of the adsorption isotherms for recombinant insulin which shows that from an initial concentration of 10 units/ml, only 60% was recoverable after 6 hours in the untreated glass vials while approximately 90% was recoverable after 6 hours in the cellobiose treated vial. The percent recovery was stable for the subsequent 27 hours.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments as illustrated herein, but is only limited by the following claims.

What is claimed is:

1. An article of manufacture which is adapted for use in contact with one or more biologically active agents, said article of manufacture being selected from the group consisting of containers, implant devices, electrodes, pumps, syringes, needles, conduits, applicators, bio/opto-electric devices, tubing, said article of manufacture comprising a surface, said surface comprising a ceramic, metal or polymer having a high surface energy wherein said surface binds to said biologically active agent or agents with a certain binding energy, the improvement comprising adsorbing directly to said surface a glassy carbohydrate film, said film consisting of an oligosaccharide selected from the group of sugars consisting of cellobiose, trehalose, isomaltose, and nystose or an allosteric effector, selected from the group consisting of pyridoxal-5-phosphate and 2,3-phosphoglycerate said glassy film having a surface energy which is below the surface energy of said surface to thereby provide a reduction in the binding energy between said surface and said biologically active agent or agents.

2. An improved article of manufacture according to claim 1 wherein said article comprises a conduit for materials which comprise a biologically active agent.

3. An improved article of manufacture according to claim 1 wherein said oligosaccharide comprises a sugar selected from the group of basic sugars consisting of cellobiose, trehalose, isomaltose, and nystose.

4. An improved article of manufacture according to claim 1 wherein said glassy film comprises an allosteric effector selected from the group consisting of pyridoxal-5-phosphate and 2,3-phosphoglycerate.

5. An improved article of manufacture according to claim 3 wherein said glassy film comprises an allosteric effector.

6. An improved article of manufacture according to claim 1 wherein said ceramic is glass.

7. An improved article of manufacture according to claim 1 wherein said article is a container for materials which comprise biologically active agents.

8. An improved article of manufacture according to claim 6 wherein said oligosaccharide is cellobiose.

* * * * *